United States Patent [19]
Lu et al.

[11] Patent Number: 5,853,740
[45] Date of Patent: Dec. 29, 1998

[54] DELIVERY SYSTEM FOR PHARMACEUTICAL AGENTS ENCAPSULATED WITH OILS

[75] Inventors: Mou-Ying Fu Lu, Lake Bluff; Akwete L. Adjei, Wadsworth; Hillard W. Johnson, Gurnee, all of Ill.

[73] Assignee: Abbott Laboratories, Abbott Park, Ill.

[21] Appl. No.: 693,724

[22] Filed: Aug. 7, 1996

[51] Int. Cl.$^6$ .................................................. A61K 9/113
[52] U.S. Cl. ........................ 424/400; 424/489; 424/490; 424/491; 514/2; 514/800; 514/938
[58] Field of Search .................. 424/489, 490, 424/491, 400; 514/2, 800, 938

[56] References Cited

U.S. PATENT DOCUMENTS 4,363,806  12/1982  Bergstrom et al. ...................... 424/241

FOREIGN PATENT DOCUMENTS

| 9622786 | of 0000 | Japan . |
| 55-82 15829 | 7/1980 | Japan . |
| 58-61830 | 4/1983 | Japan . |
| 60-166604 | 8/1985 | Japan . |
| WO 92/18827 | 10/1992 | WIPO . |
| WO 94/16682 | 4/1994 | WIPO . |
| WO 94/22414 | 10/1994 | WIPO . |
| WO 96/04894 | 2/1996 | WIPO . |

OTHER PUBLICATIONS

Patent Abstracts of Japan, vol. 15, No. 429 (1991), O. Masanori, "Hair Cosmetic Base with Sterioscopic Pattern".
Patent Abstracts of Japan, vol. 4, No. 42 (1980), M. Masakazu, "Insulin–Containing Emulsion and Its Preparation".

Biological & Pharmaceutical Bulletin, vol. 18, No. 12 (1995), pp. 1718–1723, A. Matsuzawa et al.,"Absorption of Insulin Using Water–in–Oil–In Water Emulsion from an Enteral Loop in Rats".

Lipids, vol. 27, No. 9 (1992), N. Oba et al., pp. 701–705, "Evaluation of an Oleic Acid Water–in–Oil–in–Water–Type Multiple Emulsion as Potential Drug Carrier via the Enteral Route."

Acta Diabetol. Lat., vol. 15, No. 3–4 (1978), M. Shichiri et al., pp. 175–183, "Increased Intestinal Absorption of Insulin in a Micellar Solution: Water–in–Oil–in–Water Insulin Micelles".

Pharmaceutical Sciences, vol. 1, No. 12 (1995), pp. 559–561, D.Q.M. Craig et al., "A Comparison of the Self–Emulsifying Properties of Polyglycolysed Glyceride Oils".

Florence and Whitehill, *International Journal of Pharmaceutics*, 1982, 11, 277–308.

Matsumoto, et al., *Journal of Colloid and Interface Science*, 1976, 57, 353–361.

*Primary Examiner*—Neil S. Levy
*Attorney, Agent, or Firm*—Mona Anand

[57] ABSTRACT

The present invention provides a uniform dispersion in aqueous medium of droplets comprising: (a) a core comprising water, a non-toxic $C_2$–$C_5$ alkanol, a water-soluble drug, and a surfactant, and (b) a coating surrounding the core comprising one or more pharmaceutically acceptable oils. The compositions of the present invention are particularly useful for the oral delivery of therapeutic agents because of their potential for taste masking, prolonged action, and protection of the drug against the external environment and enzyme entrapment.

11 Claims, 2 Drawing Sheets

5,853,740

DELIVERY SYSTEM FOR PHARMACEUTICAL AGENTS ENCAPSULATED WITH OILS

TECHNICAL FIELD

The present invention relates to pharmaceutical compositions and a method of preparing such compositions. More particularly, this invention concerns pharmaceutical compositions useful for the sublingual or buccal administration of water-soluble pharmaceutical agents.

BACKGROUND OF THE INVENTION

Oral administration of liquid dosage forms is a particularly useful route of administration of therapeutic agents. However, administration of many compounds by these routes is unavailable. Orally administered therapeutic agents are rapidly transported to the stomach and small intestine for absorption across the gastro-intestinal mucosal membranes into the blood. The efficiency of absorption of a therapeutic agent (i.e., the ratio of the amount entering the blood to the amount administered) following oral administration of many drugs can be low because of several factors which serve to metabolize the administered chemical. Therefore, if the choice route of administration is the oral route, it is often necessary to administer large dosages of the compounds which is costly and in many cases inefficient. Such therapeutic agents can be administered via other routes such as intravenously, subcutaneously, or intraperitoneally, but these alternatives are all invasive by nature and can involve pain and discomfort to a subject.

Oral administration in a liquid dosage form of otherwise suitable compounds may be also be impractical because of the unpalatability of the drug. Unpalatable drugs which are carried in aqueous media are tasted almost immediately upon ingestion and produce an unpleasant taste or aftertaste. Such drugs can be administered orally in suspensions wherein the drug particles are coated with a taste-masking compound, or in solid dosage forms (i.e., capsules or tablets). Coating the drug particles leads to an extra step in the manufacturing process, and pharmaceutical suspensions have other associated problems including stability and settling of the active agent. Solid dosage forms have lead to complaints among patients such as juveniles or the elderly who have difficulty swallowing capsules or tablets.

A particularly useful class of compounds are peptides of twenty or less aminoacyl residues. Recent pharmaceutical research has led to the discovery of many synthetic peptides in this class which are effective therapeutic agents. Noteworthy among these synthetic small peptides are compounds which act as either agonists or antagonists of gonadotropin releasing hormone (GnRH, also known as "luteinizing hormone releasing hormone", LHRH), and peptides or psuedo peptides of twenty residues or less which act to inhibit renin and are thus effective as agents for treating hypertension and related disease conditions of the cardiovascular system. A number of small peptides and modified peptides have also been found which act to modulate the natural peptide C5a.

While the discovery of peptide compounds having therapeutic value has moved rapidly in the last few years, the development of viable drug delivery systems for many of these compounds has often proved problematic. The gastrointestinal tract secretes a variety of agents that metabolize polypeptides. Exemplary of such catabolic agents are pepsin, trypsin, chymotrypsin, carboxypolypeptidases, aminopolypeptidases and dipeptidases. Polypeptides that escape catabolism in the stomach and small intestine are transported across the cells lining the gastrointestinal tract into the portal circulation, which carries absorbed polypeptides to the liver. Absorbed polypeptides are subject to further degradation by a myriad of hepatic metabolic events. Such hepatic degradation of absorbed materials from the blood before such materials enter the general systemic circulation is known in the pharmaceutical art as the "first pass effect". Therefore, most, if not all, of these compounds must be administered parenterally as, for example, subcutaneous, intramuscular, or intraperitoneal injection. Since most patients cannot self-administer parenteral drug formulations, it is frequently necessary that drugs of this type be administered in an out-patient setting leading to additional costs associated with their use.

There is, therefore, a pressing need for new, efficient, cost effective, and non-invasive methods and compositions for the administration to patients of therapeutic agents, particularly peptides, which are otherwise unsuitable for oral administration.

SUMMARY OF THE INVENTION

Figure 1:
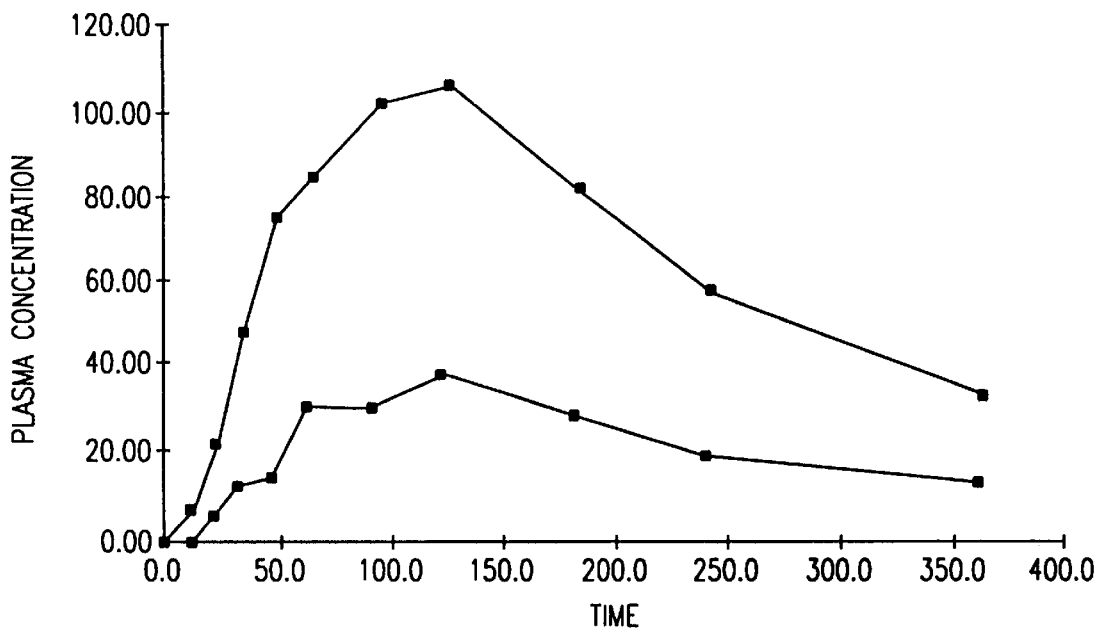
FIG. 1 is the plot of plasma concentration in ng/mL vs time in minutes following the oral administration to rats of a dose of 3 mg/kg of water-in-oil formulation AO and water-in-oil-in-water formulation A of the leutinizing hormone releasing hormone (LHRH) agent N-acetyl-D-2-naphthylalanyl-D-4-chlorophenylalanyl-D-3-pyridylalanyl-L-seryl-L-N-methyltyrosyl-D-$N^e$-nicotinoyllysyl-L-leucyl-L-$N^e$-isopropyllysyl-L-prolyl-D-alanylamide acetate. The upper curve represents formulation A and the lower curve represents formulation AO.

Multiple emulsions are particularly useful delivery systems for therapeutic agents because of their potential for taste masking, prolonged action, and protection of the drug against the external environment and enzyme entrapment. We have discovered that an active pharmaceutical agent can be encapsulated in aqueous droplets coated with a pharmaceutically acceptable oil which, when administered orally as an aqueous microemulsion, is stable to stomach acid and enzymes. Accordingly, in its principle embodiment, the present invention provides a uniform dispersion in aqueous medium of droplets comprising: (a) a core comprising water, a non-toxic $C_2$–$C_5$ alkanol, a water-soluble drug, and a surfactant, and (b) a coating surrounding the core comprising one or more pharmaceutically acceptable oils.

In another aspect, the present invention provides a method for the preparation of a uniform dispersion in aqueous medium of droplets comprising an aqueous core coated with a pharmaceutically acceptable oil comprising: (a) dissolving a water soluble drug in a co-solvent mixture comprising water and a $C_2$–$C_5$ alkanol to form a clear solution comprising 1–10 mg/mL of drug, from about 20% v/v to about 80% v/v of $C_2$–$C_5$ alkanol, and from about 80% v/v to about 20% v/v of water wherein the volume percentages are based on the total volume of the co-solvent mixture, (b) emulsifying the solution prepared in step (a) into an oil phase comprising a surfactant and a pharmaceutically acceptable oil, such that the resulting emulsion comprises from about 2% v/v to about 10% v/v $C_2$–$C_5$ alkanol, from about 10% v/v to about 2% v/v water, from about 10% v/v to about 50% v/v surfactant, and from about 20% v/v to about 50% v/v pharmaceutically acceptable oil wherein the volume percentages are based on the total volume of the resulting emulsion, and (c) dispersing the emulsion of step (b) into an aqueous solution such that the emulsion from step (b) constitutes from about 10% by volume to about 30% by volume of the resulting dispersion.

DETAILED DESCRIPTION

The compositions and methods of the present invention are suitable for the administration of a wide variety of peptide and non-peptide drugs which are soluble in water or mixtures of water and a non-toxic $C_2$–$C_5$ alkanol.

Examples of unpalatable therapeutic agents suitable for formulation in the aqueous dispersions of the present invention include the antibiotics clarithromycin and erythromycin which are valuable drugs for treating infections.

The aqueous dispersions of the present invention are particularly suited for the oral administration of peptide or psuedo-peptide therapeutic agents of twenty amino acids or less, which are normally degraded upon oral administration. As used herein the term "psuedo peptide" means a compound comprising a sequence of twenty amino acid residues or less connected by peptide linkages in which one or more of the aminoacyl units may comprise a non-naturally-occuring amino acid or a naturally-occuring amino acid which has a modified alpha side-chain. Preferably, polypeptides used in the present invention are drugs, medicaments and other agents having a pharmacological of physiological action in an animal subject to affect lutenizing hormone releasing hormone (LHRH), to inhibit the action of renin, or to modulate the physiological activity of C5a.

The medicaments useful in the compositions of the present invention include not only those specifically mentioned above, but also where appropriate the pharmaceutically acceptable salts, ester, amides, and prodrugs thereof. By "pharmaceutically acceptable salts, ester, amides, and prodrugs" is meant those carboxylate salts, amino acid addition salts, esters, amides, and prodrugs of a compound which are, within the scope of sound medical judgement, suitable for use in contact with the tissues of humans and lower animals without undue toxicity, irritation, allergic response and the like commensurate with a reasonable benefit/risk ratio and effective for their intended use. Pharmaceutically acceptable salts are well known in the art . For example, S. M Berge, et al. describe pharmaceutically acceptable salts in detail in *J. Pharmaceutical Sciences*, 1977, 66: 1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The term "prodrug" refers to compounds which are rapidly transformed in vivo to yield the parent medicinal compound, as for example, by hydrolysis in the blood. A thorough discussion is provided in T. Higuchi and V. Stella, "Pro-drugs as Novel Delivery Systems", ed. Edward B. Roche, American Pharmaceutical Association and Pergamon Press (1987).

By a "therapeutically effect amount" of a medicament is meant a sufficient amount of the compound to obtain the intended therapeutic benefit, at a reasonable benefit/risk ratio applicable to any medical treatment. It will be understood, however, that the total daily usage of the medicaments and compositions of the present invention will be decided by the attending physician with the scope of sound medical judgement. The specific therapeutically effective dose level for any particular patient will depend upon a variety of factors including the disorder being treated and the severity of the disorder; activity of the compound employed; the specific composition employed; the age, body weight, general health, sex and diet of the patient; the time of administration, route of administration and rate of excretion of the specific compound employed; the duration of the treatment; drugs used in combination or coincidental with the specific compound employed; and like factors well known in the medical arts. For example, it is well within the skill of the art to start at doses lower than required to achieve the desired therapeutic effect and to gradually increase the dosage until the desired effect is achieved.

The preparation and therapeutic use of suitable peptide agonists and antagonists of LHRH comprising from three to ten aminoacyl residues for incorporation into microemulsions in accordance with the present invention are disclosed in the following United States Patents which are incorporated herein by reference:

1. Folkers, et al., U.S. Pat. No. 3,787,385, issued Jan. 22, 1974;
2. Flouret, et al., U.S. Pat. No. 3,790,555, issued Feb. 8, 1974;

3. Flouret, U.S. Pat. No. 3,826,794, issued Jul. 30, 1974;
4. Fujino, et al., U.S. Pat. No. 3,853,837, issued Dec. 10, 1974;
5. Sakakibara, et al., U.S. Pat. No. 3,880,825, issued Apr. 29, 1975;
6. Shields, U.S. Pat. No. 3,915,947, issued Oct. 28, 1975;
7. Folkers, et al., U.S. Pat. No. 3,953,416, issued Apr. 27, 1976;
8. Hoffmann, et al., U.S. Pat. No. 3,963,691, issued Jun. 15, 1976;
9. Folkers, et al., U.S. Pat. No. 3,974,135, issued Aug. 10, 1976;
10. Koenig, et al., U.S. Pat. No. 4,003,884, issued Jan. 18, 1977;
11. Fujino, et al., U.S. Pat. No. 4,008,209, issued Feb. 15, 1977;
12. Tinney, et al., U.S. Pat. No. 4,022,759, issued May 10, 1977;
13. Tinney, U.S. Pat. No. 4,022,760, issued May 10, 1977;
14. Tinney, et al., U.S. Pat. No. 4,022,761, issued May 10, 1977;
15. Johnson, et al., U.S. Pat. No. 4,071,622, issued Jan. 31, 1978;
16. Koenig, U.S. Pat. No. 4,024,248, issued May 17, 1977;
17. Amoss, et al., U.S. Pat. No. 4,072,668, issued Feb. 7, 1978;
18. Tinney, U.S. Pat. No. 4,075,189, issued Feb. 21, 1978;
19. Nicolaides, U.S. Pat. No. 4,075,192, issued Feb. 21, 1978;
20. Tinney, U.S. Pat. No. 4,087,419, issued May 2, 1978;
21. Foel, et al., U.S. Pat. No. 4,089,946, issued May 16, 1978;
22. Dutta, et al., U.S. Pat. No. 4,100,274 issued Jul. 11, 1978;
23. Moody, U.S. Pat. No. 4,128,638, issued Dec. 5, 1978;
24. Fujino, et al., U.S. Pat. No. 4,229,438, issued Oct. 21, 1980;
25. Nestor, et al., U.S. Pat. No. 4,234,571, issued Nov. 18, 1980;
26. Rivier, et al., U.S. Pat. No. 4,344,946, issued Jan. 13, 1981;
27. Sarantakis, U.S. Pat. No. 4,253,997, issued Mar. 3, 1981;
28. Coy, et al., U.S. Pat. No. 4,317,815, issued Mar. 2, 1982;
29. Nestor, et al., U.S. Pat. No. 4,318,905, issued Mar. 9, 1982;
30. Nestor, et al., U.S. Pat. No. 4,341,767, issued Jul. 27, 1982; 35 31.
31. Veber, et al., U.S. Pat. No. 4,377,515, issued Mar. 22, 1983;
32. Rivier, et al., U.S. Pat. No. 4,382,922, issued May 10, 1983;
33. Rivier, et al., U.S. Pat. No. 4,409,208, issued Oct. 11, 1983;
34. Vail, Jr., et al., U.S. Pat. No. 4,410,514, issued Oct. 18, 1983;
35. Nestor, et al., U.S. Pat. No. 4,419,347, issued Dec. 6, 1983;
36. Sherwood, et al., U.S. Pat. No. 4,443,368, issued Apr. 17, 1984;
37. Rivier, et al., U.S. Pat. No. 4,444,759, issued Apr. 24, 1984;
38. Nestor, et al., U.S. Pat. No. 4,481,190, issued Nov. 6, 1984;
39. Folkers, et al., U.S. Pat. No. 4,504,414, issued Mar. 12, 1985;
40. Nestor, et al., U.S. Pat. No. 4,530,920, issued Jul. 23, 1985;
41. Roeske, U.S. Pat. No. 4,547,370, issued Oct. 15, 1985;
42. Antoni, et al., U.S. Pat. No. 4,552,864, issued Nov. 12, 1985;
43. Rivier, et al., U.S. Pat. No. 4,565,804, issued Jan. 21, 1986;
44. Rivier, et al., U.S. Pat. No. 4,569,927, issued Feb. 11, 1986;
45. Seproedi, et al., U.S. Pat. No. 4,600,705, issued Jul. 15, 1986;
46. Mia, U.S. Pat. No. 4,608,251, issued Aug. 26, 1986;
47. Vale, Jr., et al., U.S. Pat. No. 4,619,914, issued Oct. 28, 1986;
48. Folkers, et al., U.S. Pat. No. 4,642,332, issued Feb. 10, 1987;
49. Gulyas, et al., U.S. Pat. No. 4,647,553, issued Mar. 3, 1987;
50 Rivier, et al., U.S. Pat. No. 4,652,550, issued Mar. 24, 1987;
51. Folkers, et al., U.S. Pat. No. 4,656,247, issued Apr. 7, 1987;
52. Rivier, et al., U.S. Pat. No. 4,661,472, issued Apr. 28, 1987;
53. Nestor, et al., U.S. Pat. No. 4,667,014, issued May 10, 1987;
54. Rivier, et al., U.S. Pat. No. 4,677,193, issued Jun. 30, 1987;
55. Roeske, et al., U.S. Pat. No. 4,689,396, issued Aug. 25, 1987;
56. Nestor, et al., U.S. Pat. No. 4,690,916, issued Sep. 1, 1987;
57. Uhmann, et al., U.S. Pat. No. 4,691,008, issued Sep. 1, 1987;
58. Folkers, et al., U.S. Pat. No. 4,721,775, issued Jan. 26, 1988;
59. Schally, et al., U.S. Pat. No. 4,725,577, issued Feb. 16, 1988;
60. Vale, Jr., et al., U.S. Pat. No. 4,740,500, issued Apr. 26, 1988;
61. Gulyas, et al., U.S. Pat. No. 4,758,552, issued Jul. 19, 1988;
62. Schally, et al., U.S. Pat. No. 4,800,191, issued Jan. 24, 1989;
63. Nestor, et al., U.S. Pat. No. 4,801,577, issued Jan. 31, 1989;
64. Folkers, et al., U.S. Pat. No. 4,935,491, issued Jan. 19, 1990;
65. Seproedi, et al., U.S. Pat. No. 4,948,873, issued Aug. 14, 1990;
66. Haviv, et al., U.S. Pat. No. 5,110,904, issued May 5, 1992;
67. Haviv, et al., U.S. Pat. No. 5,140,009, issued Aug. 18, 1992; and
68. Schally, et al., U.S. Pat. No. 5,198,533, issued Mar. 30, 1993.

Particularly preferred LHRH-active peptides and psuedopeptides for inclusion in formulations of the present invention include the following compounds and their pharmaceutically acceptable salts:

N-acetyl-D-2-naphthylalanyl-D-4-chlorophenylalanyl-D-3-pyridylalanyl-L-seryl-L-N-methyltyrosyl-D-N$^e$-nicotinoyllysyl-L-leucyl-L-N$^e$-isopropyllysyl-L-prolyl-D-alanylamide acetate, disclosed in U.S. Pat. No. 5,110,904, 5-oxo-L-prolyl-L-histidyl-L-tryptophanyl-L-seryl-L-tyrosyl-D-leuyl-L-leuyl-L-arginyl-L-prolylethylamide, also known by the generic name leuprolide, disclosed in U.S. Pat. No. 4,005,063, and N-(S)-tetrahydrofur-2-oyl-glycyl-D-(3-(napth-2-yl)alanyl)-D-(3-(4-chlrophenyl)alanyl)-D-3-(pyrid-3-yl)alanyl-seryl-N-methyltyrosyl-(N$^e$-nicotinyl)lysyl-leucyl-(N$^e$-isopropyl)lysyl-prolyl-D-alanylamide, disclosed in U.S. Pat. No. 5,502,035 which is incorporated herein by reference.

Renin inhibitor compounds suitable for incorporation into formulations in accordance with the present invention are disclosed in the following United States Patents which are incorporated herein by reference:

69. Veber, et al., U.S. Pat. No. 4,384,994, issued May 24, 1983;
70. Boger, et al., U.S. Pat. No. 4,470,971, issued Sep. 11, 1984;
71. Boger, et al., U.S. Pat. No. 4,477,440, issued Oct. 16, 1984;
72. Boger, et al., U.S. Pat. No. 4,477,441, issued Oct. 16, 1984;
73. Vebner, et al., U.S. Pat. No. 4,474,941, issued Oct. 30, 1984;
74. Veber, et al., U.S. Pat. No. 4,478,826, issued Oct. 23, 1984;
75. Cazaubon, et al., U.S. Pat. No. 4,481,192, issued Nov. 6, 1984;
76. Boger, et al., U.S. Pat. No. 4,485,099, issued Nov. 27, 1984;
77. Hansen, et al., U.S. Pat. No. 4,510,085, issued Apr. 9, 1985;
78. Hansen, et al., U.S. Pat. No. 4,514,332, issued Apr. 30, 1985;
79. Matsueda, et al., U.S. Pat. No. 4,548,926, issued Oct. 22, 1985;
80. Pinori, et al., U.S. Pat. No. 4,560,505, issued Dec. 24, 1985;
81. Riniker, et al., U.S. Pat. No. 4,595,677, issued Jun. 17, 1986;
82. Hoover, U.S. Pat. No. 4,599,198, issued Jul. 8, 1986;
83. Evans, et al., U.S. Pat. No. 4,609,641, issued Sep. 2, 1986;
84. Szelke, et al., U.S. Pat. No. 4,609,643, issued Sep. 2, 1986;
85. Fuhrer, et al., U.S. Pat. No. 4,613,676, issued Sep. 23, 1986;
86. Ryono, et al., U.S. Pat. No. 4,616,088, issued Oct. 7, 1986;
87. Ryono, et al., U.S. Pat. No. 4,629,724, issued Dec. 16, 1986;
88. Bock, et al., U.S. Pat. No. 4,636,491, issued Nov. 3, 1987;
89. Luly, et al., U.S. Pat. No. 4,645,759, issued Feb. 24, 1987;
90. Szelke, et al., U.S. Pat. No. 4,650,661, issued Mar. 17, 1987;
91. Luly, et al., U.S. Pat. No. 4,652,551, issued Mar. 24, 1987;
92. Izuka, et al., U.S. Pat. No. 4,656,269, issued Apr. 7, 1987;
93. Baran, et al., U.S. Pat. No. 4,657,931, issued Apr. 14, 1987;
94. Boger, et al., U.S. Pat. No. 4,661,473, issued Apr. 28, 1987;
95. Bock, et al., U.S. Pat. No. 4,663,310, issued May 5, 1987;
96. Boger, et al., U.S. Pat. No. 4,665,052, issued May 12, 1987;
97. Evans, et al., U.S. Pat. No. 4,665,055, issued May 12, 1987;
98. Ryono, et al., U.S. Pat. No. 4,665,193, issued May 12, 1987;
99. Raddatz, et al., U.S. Pat. No. 4,666,888, issued May 19, 1987;
100. Boger, et al., U.S. Pat. No. 4,668,663, issued May 26, 1987;
101. Boger, et al., U.S. Pat. No. 4,668,770, issued May 26, 1987;
102. Hoover, U.S. Pat. No. 4,668,769, issued May 26, 1987;
103. Luly, et al., U.S. Pat. No. 4,680,284, issued Jul. 14, 1987;
104. Yamato, et al., U.S. Pat. No. 4,683,220, issued Jul. 28, 1987;
105. Matsueda, et al., U.S. Pat. No. 4,698,329, issued Oct. 6, 1987;
106. Thaisrivongs, U.S. Pat. No. 4,703,846, issued Nov. 10, 1987;
107. Holzman, et al., U.S. Pat. No. 4,709,010, issued Nov. 27, 1987;
108. Izuka, et al., U.S. Pat. No. 4,711,958, issued Dec. 8, 1987;
109. Szelke, et al., U.S. Pat. No. 4,713,445, issued Dec. 15, 1987;
110. Raddatz, et al., U.S. Pat. No. 4,721,776, issued Jan. 26, 1988;
111. Hansen, et al., U.S. Pat. No. 4,722,922, issued Feb. 2, 1988;
112. Wagnon, et al., U.S. Pat. No. 4,725,580, issued Feb. 16, 1988;
113. Luly, et al., U.S. Pat. No. 4,725,583, issued Feb. 16, 1983;
114. Luly, et al., U.S. Pat. No. 4,725,584, issued Feb. 16, 1983;
115. Buhlmayer, et al., U.S. Pat. No. 4,727,060, issued Feb. 23, 1988;
116. Bindra, et al., U.S. Pat. No. 4,729,985, issued Mar. 8, 1988;
117. Hudspeth, et al., U.S. Pat. No. 4,735,933, issued Apr. 5, 1988;
118. Boger, U.S. Pat. No. 4,743,584, issued May 10, 1988;
119. Hudspeth, et al., U.S. Pat. No. 4,743,585, issued May 10, 1988;
120. Wagnon, et al., U.S. Pat. No. 4,746,648, issued May 24, 1988;

121. Bindra, et al., U.S. Pat. No. 4,749,687, issued Jun. 7, 1988;
122. Gordon, U.S. Pat. No. 4,749,781, issued Jun. 7, 1988;
123. Raddatz, et al., U.S. Pat. No. 4,755,592, issued Jul. 5, 1988;
124. Natarajan, et al., U.S. Pat. No. 4,757,050, issued Jul. 12, 1988;
125. Buhlmayer, et al., U.S. Pat. No. 4,758,584, issued Jul. 19, 1988;
126. Kaltenbronn, et al., U.S. Pat. No. 4,804,743, issued Feb. 14, 1989
127. Boger, et al., U.S. Pat. No. 4,812,442, issued Mar. 14, 1989;
128. Raddatz, et al., U.S. Pat. No. 4,812,555, issued Mar. 14, 1989;
129. Hoover, et al., U.S. Pat. No. 4,814,342, issued Mar. 21, 1989;
130. Bender, et al., U.S. Pat. No. 4,818,748, issued Apr. 4, 1989;
131. Patel, U.S. Pat. No. 4,820,691, issued Apr. 11, 1989;
132. Luly, et al., U.S. Pat. No. 4,826,815, issued May 2, 1989;
133. Sham, U.S. Pat. No. 4,826,958, issued May 2, 1989;
134. Raddatz, et al., U.S. Pat. No. 4,829,053, issued May 9, 1989;
135. Rosenberg, et al., U.S. Pat. No. 4,837,204, issued Jun. 6, 1989;
136. Patchett, et al., U.S. Pat. No. 4,839,357, issued Jun. 13, 1989;
137. Wagnon, et al., U.S. Pat. No. 4,840,935, issued Jun. 20, 1989;
138. Iizuka, et al., U.S. Pat. No. 4,841,067, issued Jun. 20, 1989;
139. Luly, et al., U.S. Pat. No. 4,845,079, issued Jul. 4, 1989;
140. Iizuka, et al., U.S. Pat. No. 4,853,463, issued Aug. 1, 1989;
141. Wanger, et al., U.S. Pat. No. 4,855,286, issued Aug. 8, 1989;
142. Hoover, U.S. Pat. No. 4,855,303, issued Aug. 8, 1989;
143. Rosenberg, et al., U.S. Pat. No. 4,857,507, issued Aug. 15, 1989;
144. Hoover, et al., U.S. Pat. No. 4,859,654, issued Aug. 22, 1989;
145. Fuhrer, et al., U.S. Pat. No. 4,863,903, issued Sep. 5, 1989;
146. Iizuka, et al., U.S. Pat. No. 4,863,904, issued Sep. 15, 1989;
147. Hudspeth, et al., U.S. Pat. No. 4,863,905, issued Sep. 15, 1989;
148. Thaisrivongs, et al., U.S. Pat. No. 4,864,017, issued Sep. 5, 1989;
149. Huang, et al., U.S. Pat. No. 4,874,745, issued Oct. 17, 1989;
150. Hester, et al., U.S. Pat. No. 4,880,781, issued Nov. 14, 1989;
151. Hudspeth, et al., U.S. Pat. No. 4,895,834, issued Jan. 23, 1990; and
152. Fung, et al., U.S. Pat. No. 5,268,374, issued Dec. 7, 1993.

Preferred renin inhibitors for incorporation into the formulations of the present invention include:

H-((beta,beta, dimethyl)beta-Ala-4-(CH$_3$O)-Phe-His-(2S-amino-1-cyclohexyl-3R,4S-dihydroxy-6-methylheptane, also known by the generic name enalkiren, disclosed in U.S. Pat. No. 4,845,079, 2S-2-benzyl-3-((1-methylpiperazin-4-yl)sulfonyl)propionyl-4-thial-(2S-amino-1-cyclohexyl-3R,4S-dihydroxy-6-methylheptane, also known by the generic name zankiren, disclosed in published European Patent Application No. EP 456 189, published Nov. 13, 1991, 2S,1S-(4-methoxymethoxypiperidin-1-yl)carbonyl-2-phenyl-ethoxyhexanoic acid amide of 3-(4-morpholinyl)propyl-5S-amino-6-cyclohexyl-4S-hydroxy-2S-isopropylhexanamide, disclosed in U.S. Pat. No. 5,268,374, and N-(1S)-(4-(methoxymethoxypiperidin-1-yl)carbonyl)-2-phenylethyl-L-norleucyl amide of 3-(4-morpholinyl)propyl-5S-amino-6-cyclohexyl-4S-hydroxy-2S-isopropylhexanamide, disclosed in U.S. Pat. No. 5,268,374.

C5a agonists and antagonists suitable for incorporation into formulations in accordance with the present invention are disclosed in the following United States Patents which are incorporated herein by reference:

153. Hahn, U.S. Pat. No. 4,692,511 issued Sep. 8, 1987;
154. Luly, et al., U.S. Pat. No. 5,190,922 issued Mar. 2, 1993; and
155. Kawai, et al., U.S. Pat. No. 5,223,485 issued Jun. 29, 1993.

The compositions of the present invention provide a uniform dispersion in aqueous medium of droplets wherein the droplets comprise from about 10% to about 30% of the total volume of the dispersion. Without being limited by theory, it is believed that the compositions of the present invention are water-in-oil-in-water microemulsions of the so-called Type A variety in which each water droplet is surrounded by a thin oil layer, in turn uniformly dispersed in water. See Florence, A. T. and Whitehill, D., *International Journal of Pharmaceutics*, 1982, 11, 277–308. The compositions are translucent or transparent in appearance and do not separate on standing. The droplets are less than one micron and preferably from about 50 nM to about 200 nM in diameter. The external aqueous phase may contain a hydrophilic non-ionic surfactant in a concentration of from about 2% to about 20% by volume based on the total volume of the microemulsion to increase its viscosity and promote microemulsification. Representative surfactants have a hydrophilic lipophilic balance (HLB value) of between about 8 and about 18. Examples of suitable surfactants include the lecithins, sorbitan mololaurate, polyoxyethyllene-4-lauryl ether, polyethylene glycol 400 monostearate, polyoxyethylene-20-sorbitan monooleate, polyoxyethylene-4-sorbitan monolaurate, polyoxyethylene-20-sorbitan monopalmitate, polyoxyethylene-20-sorbitan monolaurate, and polyoxyethylene-40-stearate. Egg lecithin is particularly preferred.

The droplets comprise a therapeutically effective amount of a water-soluble drug as described above, between about 2% v/v to about 10% v/v of a non-toxic $C_2$–$C_5$ alkanol, between about 10% v/v to about 50% v/v of non-ionic lipophilic surfactant, between about 20% v/v to about 50% v/v pharmaceutically acceptable oil, and between about 2% v/v to about 10% v/v water based upon the volume of the droplet. Non-toxic $C_2$–$C_5$ alcohols useful in the compositions of the present invention are selected from those well-known in the art and include ethanol, isopropanol, and the like. Non-toxic alcohols for use in pharmaceutical formulations are well-known in the art (cf., for example, "Handbook of Pharmaceutical Excipients". pub. by the American Pharmaceutical Association and the Pharmaceutical Society of Great Britain (1986)). Preferably the non-toxic $C_2$–$C_5$ alcohol is ethanol.

Non-ionic, lipophilic surfactants are used to promote emulsification of the aqueous phase into the oil phase. Representative surfactants include oleic acid (9-octadecanoic acid), Laureth 9 (polyethylene glycol lauryl ether), Labrafac 10M (saturated polyglycolized $C_8$–$C_{10}$ glycerides, HLB 10), Labrafil M1944 (Unsaturated polyglycolized glycerides, HLB 4), Labrasol (saturated polyglycolized $C_8$–$C_{10}$ glycerides, HLB 14), sorbitan monooleate, propylene glycol monolaurate, sorbitan monostearate, glyceryl monostearate and the like. Preferred surfactants have a HLB value of between about 4 and about 6 and include Labrafil M1944, sorbitan mono-oleate, propylene glycol monolaurate, sorbitan monostearate, glyceryl monostearate and the like. The most preferred surfactants are oleic acid and Laureth 9.

The pharmaceutically acceptable oils suitable for use in droplet formation comprise oils that are considered safe for human consumption and are relatively stable. Furthermore, the oil should not be incompatable with the drug being delivered. Suitable pharmaceutically acceptable oils include mineral oil, Neobee® oil, peanut oil, soybean oil, safflower oil, corn oil, and olive oil. Olive oil is particularly preferred.

The droplets may further comprise an ion-pair forming reagent wherein the mole ratio of ion-pair forming reagent to drug is from about 2:1 to about 10:1. The ion-pair forming reagent is added to increase the lipophilicity of the dissolved drug and thereby increase its membrane permeability. Increasing the drug's lipophilicity may also provide some protection of the drug from enzymatic deactivation as much of the peptide degradation that occurs in vivo does so in the aqueous environment of the gastrointestinal tract. Representative ion-pair forming reagents include sodium decanesulfonate, sodium lauryl sulfate, and sodium benzoate. Especially preferred is sodium decanesulfonate in a mole ratio of ion-pair forming reagent to drug is of about 5:1.

The droplets may optionally comprise from about 5% to about 10% based on the total volume of the droplet of an oral mucosal membrane transport enhancing agent. Such agents facilitate the absorption of the therapeutic agent across the mucosal tissues in the oral cavity and directly into the bloodstream of the subject. Tissue transport enhancing agents suitable for use in the present compositions are selected from essential or volatile oils or from non-toxic, pharmaceutically acceptable organic and inorganic acids. Essential or volatile oils which may be employed in the compositions are selected from peppermint oil, spearmint oil, menthol, pepper oil, eucalyptus oil, cinnamon oil, ginger oil, fennel oil, dill oil and the like. The preferred essential oil is peppermint oil.

The droplets may also contain additional agents such as preservatives and antioxidants. Typical preservatives include sodium benzoate, sorbic acid, and the methyl and propyl esters of p-hydroxy-benzoic acid (parabens). Representative antioxidants include butylated hydroxy anisole, butylated hydroxy toluene, nordihydroguaiaretic acid, the gallates such as propyl gallate, hydroquinone, propenyl methyl guaethol and alkyl thiopropionates, or water soluble agents such as alkanolamines, alcohols, and propylene glycol. The most preferred antioxidant is Tenox GT1 (1:1 vitamin E-soybean oil), present in a concentration of between about 5% to about 25% based on the total volume of the droplet.

In one preferred embodiment, the droplets comprise:

| | |
|---|---|
| Drug: | 5 mg/mL; |
| Sodium decanesulfonate: | 4.0 mg/mL; |
| Ethanol: | 10%; |
| Oleic acid: | 40%; |
| Peppermint oil: | 10%; |
| Vitamin E: | 8.0%; |
| Soybean oil: | 8.0%; |
| Olive Oil: | 22%; and |
| Water: | 2.0%. |

In another preferred embodiment, the droplets comprise:

| | |
|---|---|
| Drug: | 5 mg/mL; |
| Sodium decanesulfonate: | 4.0 mg/mL; |
| Ethanol: | 10%; |
| Laureth: | 20%; |
| Peppermint oil: | 10%; |
| Vitamin E: | 8.0%; |
| Soybean oil: | 8.0%; |
| Olive oil: | 42%; and |
| Water: | 2.0%. | wherein the drug is N-acetyl-D-2-naphthylalanyl-D-4-chlorophenyl-alanyl-D-3-pyridylalanyl-L-seryl-L-N-methyltyrosyl-D-$N^e$-nicotinoyllysyl-L-leucyl-L-$N^e$-isopropyllysyl-L-prolyl-D-alanylamide acetate.

In yet another preferred embodiment, the droplets comprise:

| | |
|---|---|
| Leuprolide acetate: | 5 mg/mL; |
| Ethanol: | 10%; |
| Oleic acid: | 40%; |
| Peppermint oil: | 10%; and |
| Vitamin E: | 8%; |
| Soybean oil: | 8%; |
| Olive oil: | 22%; and |
| Water: | 2%. |

The compositions of the present invention are prepared by:

1. Forming a water-in-oil emulsion comprising 1–10 mg/mL of drug, from about 2% v/v to about 10% v/v $C_2$–$C_5$ alkanol, from about 10% v/v to about 2% v/v water, from about 10% v/v to about 50% v/v surfactant, and from about 20% v/v to about 50% v/v pharmaceutically acceptable oil wherein the volume percentages are based on the total volume of the resulting emulsion; and 2. dispersing from about 10% by volume to about 30% by volume, based on the volume of the resulting dispersion, of the water-in-oil emulsion into an aqueous phase to form a water-in-oil-in-water microemulsion.

The water-in-oil emulsion is prepared by dissolving the drug in a co-solvent mixture of ethanol and water. If desired, an ion-pair forming reagent such as sodium decanesulfonate may be dissolved in the aqueous solution. The aqueous solution is then dispersed into an oil phase comprising relative amounts of surfactant, oral mucosal membrane transport enhancing agent, stabilizer, and pharmaceutically acceptable oil deemed sufficient to impact on drug permeation through absorption barriers. Emusification is accomplished by blending the 2-phase mixture to form an interface between the oily and aqueous phases. This blending can be accomplished using a variety of equipment including agitators, homgenizers, colloid mills, jet mixers, and ultrasonic devices. See *Remington's Pharamaceutical Sciences*, (18th. ed., 1990), pp 1537–39, and references cited therein. A particularly preferred apparatus for emulsification is a microfluidizer such as the Microfluidizer Model 1108 (Microfluidics Corp., Newton, Mass.). The microfluidizer can be used to produce the final emulsion, or an emulsion can be repeatedly passed through the homogenizer to decrease particle size to the desired range. All water-in-oil emulsions are transparent in physical appearance.

The water-in-oil-in-water microemulsions are then prepared by dispersing the desired amount of the water-in-oil emulsion prepared above in an aqueous phase comprising water and surfactant. In the most preferred embodiment, 2 parts by volume of the water-in-oil emulsion prepared above is blended with 8 parts by volume of an aqueous phase comprising water and 5% by volume of egg lecithin. The mixture was then emulsified as described above, with additional passes through the microfluidizer to reduce the mean particle size of the dispersed phase to between about 50 nM and about 200 nM in diameter, and to further improve the physical uniformity of the microemulsion. Formulation pH was adjusted to 6–7 with sodium hydroxide before homogenization.

The following Examples are provided to enable one skilled in the art to practice the invention and are merely illustrative of the invention. They should not be read as limiting the scope of the invention as defined in the claims.

EXAMPLE 1

Preparation of Microemulsion Formulations

Step 1: Preparation of Water-in-oil Emulsion (Formulation AO)

To a solution of N-acetyl-D-2-naphthylalanyl-D-4-chlorophenylalanyl-D-3-pyridylalanyl-L-seryl-L-N-methyltyrosyl-D-$N^e$-nicotinoyllysyl-L-leucyl-L-$N^e$-isopropyllysyl-L-prolyl-D-alanylamide acetate (50 mg) and sodium decanesulfonate (40 mg) dissolved in ethanol (1.0 mL) and deionized water (0.2 mL) was added oleic acid (4.0 mL) and the solution was mixed well. To the solution was added olive oil (1.0 mL) and peppermint oil (1.0 mL), and the mixture was emulsified using a microfluidizer. Tenox GT-1 (vitamin E and soybean oil, 1.6 mL) was then added to stabililze the emulsion which had a volume of 10 mL and a drug concentration 5mg/mL.

Step 2: Preparation of Water-in-oil-in-Water Emulsion A (Formulation A)

To 16 mL of an aqueous solution of egg lecithin (5% lecithin by volume, pH=10) was added 4 mL of the water-in-oil emulsion prepared in step 1. The mixture was emulsified and the particle size reduced to 50–200 nM by 5 passes through a microfluidizer to give the water-in-oil-in-water microemulsion (20 mL, drug concentration 1 mg/mL).

The formulations listed in Table 1 were prepared as described above for formulations AO and A. The drug in formulations AO-G is N-acetyl-D-2-naphthylalanyl-D-4-chlorophenylalanyl-D-3-pyridylalanyl-L-seryl-L-N-methyltyrosyl-D-$N^e$-nicotinoyllysyl-L-leucyl-L-$N^e$-isopropyllysyl-L-prolyl-D-alanylamide acetate. The drug in formulations HO and H is leuprolide acetate.

TABLE 1

Composition of Water-in-Oil Microemulsions and Water-in-Oil-in-Water Microemulsions

| Formulation | AO | A |
|---|---|---|
| Drug | 5 mg/mL | 1.0 mg/mL |
| sodium decanesulfonate | 4.0 mg/mL | 0.8 mg/mL |
| Egg lecithin | | 40 mg/mL |
| Ethanol | 10% | 2.0% |
| Oleic acid | 40% | 8.0% |
| Peppermint oil | 10% | 2.0% |
| Vitamin E | 8.0% | 1.6% |
| Soybean oil | 8.0% | 1.6% |
| Olive oil | 22% | 4.4% |
| Water | 2.0% | 80.4% |

| Formulation | BO | B |
|---|---|---|
| Drug | 5 mg/mL | 1.0 mg/mL |
| Sodium decanesulfonate | 4.0 mg/mL | 0.8 mg/mL |
| Egg lecithin | | 40 mg/mL |
| Ethanol | 10% | 2.0% |
| Laureth | 20% | 4.0% |
| Peppermint oil | 10% | 2.0% |
| Vitamin E | 8.0% | 1.6% |
| Soybean oil | 8.0% | 1.6% |
| Olive oil | 42% | 8.4% |
| Water | 2.0% | 80.4% |

| Formulation | CO | C |
|---|---|---|
| Drug | 5 mg/mL | 1.0 mg/mL |
| Sodium decanesulfonate | 4.0 mg/mL | 0.8 mg/mL |
| Egg lecithin | | 40 mg/mL |
| Ethanol | 10% | 2.0% |
| Labrafac CM10 | 40% | 8.0% |
| Peppermint oil | 10% | 2.0% |
| Vitamin E | 8.0% | 1.6% |
| Soybean oil | 8.0% | 1.6% |
| Olive oil | 22% | 4.4% |
| Water | 2.0% | 80.4% |

| Formulation | DO | D |
|---|---|---|
| Drug | 5 mg/mL | 1.0 mg/mL |
| Egg lecithin | | 40 mg/mL |
| Ethanol | 10% | 2.0% |
| Oleic acid | 40% | 8.0% |
| Peppermint oil | 10% | 2.0% |
| Vitamin E | 8.0% | 1.6% |
| Soybean oil | 8.0% | 1.6% |
| Olive oil | 22% | 4.4% |
| Water | 2.0% | 80.4% |

| Formulation | EO | E |
|---|---|---|
| Drug | 5 mg/mL | 1.0 mg/mL |
| Egg lecithin | | 40 mg/mL |
| Ethanol | 10% | 2.0% |
| Laureth-9 | 20% | 4.0% |
| Peppermint oil | 10% | 2.0% |
| Vitamin E | 8.0% | 1.6% |
| Soybean oil | 8.0% | 1.6% |
| Olive oil | 42% | 8.4% |
| Water | 2.0% | 80.4% |

| Formulation | FO | F |
|---|---|---|
| Drug | 5 mg/mL | 1.0 mg/mL |
| Sodium decanesulfonate | 4.0 mg/mL | 0.8 mg/mL |
| Egg lecithin | | 40 mg/mL |
| Ethanol | 10% | 2.0% |
| Oleic acid | 40% | 8.0% |
| Peppermint oil | 10% | 2.0% |
| Vitamin E | 8.0% | 1.6% |
| Soybean oil | 8.0% | 1.6% |
| Labrafil MI 944 | 22% | 4.4% |
| Water | 2.0% | 80.4% |

TABLE 1-continued

Composition of Water-in-Oil Microemulsions
and Water-in-Oil-in-Water Microemulsions

| Formulation | GO | G |
|---|---|---|
| Drug | 5 mg/mL | 1.0 mg/mL |
| Sodium decanesulfonate | 4.0 mg/mL | 0.8 mg/mL |
| Egg lecithin | | 40 mg/mL |
| Ethanol | 10% | 2.0% |
| Labrasol | 40% | 8.0% |
| Peppermint oil | 10% | 2.0% |
| Vitamin E | 8.0% | 1.6% |
| Soybean oil | 8.0% | 1.6% |
| Olive oil | 22% | 4.4% |
| Water | 2.0% | 80.4% |

| Formulation | HO | H |
|---|---|---|
| Drug | 5 mg/mL | 1.0 mg/mL |
| Egg lecithin | | 40 mg/mL |
| Ethanol | 10% | 2.0% |
| Oleic acid | 40% | 8.0% |
| Peppermint oil | 10% | 2.0% |
| Vitamin E | 8.0% | 1.6% |
| Soybean oil | 8.0% | 1.6% |
| Olive oil | 22% | 4.4% |
| Water | 2.0% | 80.4% |

EXAMPLE 2

Oral Drug Bioavailability of the Microemulsion Formulations in Sprague Dawley Rats Castrate male Sprague-Dawley rats, each weighing 200–225 g, were held for three weeks after surgery before shipment. The rats weighed about 300 g at the time of the experiments. Each rat was fasted overnight. A dose of 3 mg-kg of the indicated microemulsion was administered by gavage using intubation of formulations into the stomach. About 0.5 mL blood samples were collected under ether anesthesia via jugular venipuncture. Up to 12 samples (about 6 mL total) were removed from each rat. Blood samples were placed into microcentrifuge tubes containing 50 uL of 15% K3EDTA as anticoagulant. Samples were then mildly agitated by shaking and spun down for ten minutes at 5000 rpm in a Beckman Microfuge-12. Blood samples were collected prior to dosing and also at 10, 20, 30, 45, 60, 90, 120, 180, 240, and 360 minutes after dosing. Plasma samples were frozen at −10° to −20° C. until assayed. Drug concentrations in plasma samples were measured by radio-immunoassay.

Bioavailability is calculated and expressed either in terms of Area Under Curve (AUC) or as percent bioavailability. AUC is determined by calculating the are under the curve of plots of time (X-axis) versus plasma concentration (Y-axis) of the administered drug. Typically, AUC is determined over a 6 (0–6) hour period. Percent bioavailability is calculated as the ratio $$\frac{AUC \text{ for oral administration}}{AUC \text{ for the same dose administered } iv} \times 100$$

The AUC and oral bioavailability for representative formulations is summarized in Table 2. Control is a saline solution of N-acetyl-D-2-naphthylalanyl-D-4-chlorophenylalanyl-D-3-pyridylalanyl-L-seryl-L-N-methyltyrosyl-D-$N^e$-nicotinoyllysyl-L-leucyl-L-$N^e$-isopropyllysyl-L-prolyl-D-alanylamide acetate or leuprolide acetate.

TABLE 2

Oral Drug Bioavailability in Sprague Dawley Rats

| Formulation | AUC | % Bioavailability |
|---|---|---|
| Control | 161 | 0.05 |
| A | 24944 | 8.31 |
| B | 50440 | 16.81 |
| C | 1808 | 0.60 |
| E | 1454 | 0.48 |
| F | 9198 | 3.07 |
| G | 396 | 0.13 |
| H | 13714 | 4.57 |

The data summarized in Table 2 demonstrates the increased oral bioavailability of water-in-oil-in-water emulsions of the present invention over aqueous solutions.

EXAMPLE 3

Comparison of Water-in-Oil and Water-in-Oil-in-Water Emulsions

Figure 2:
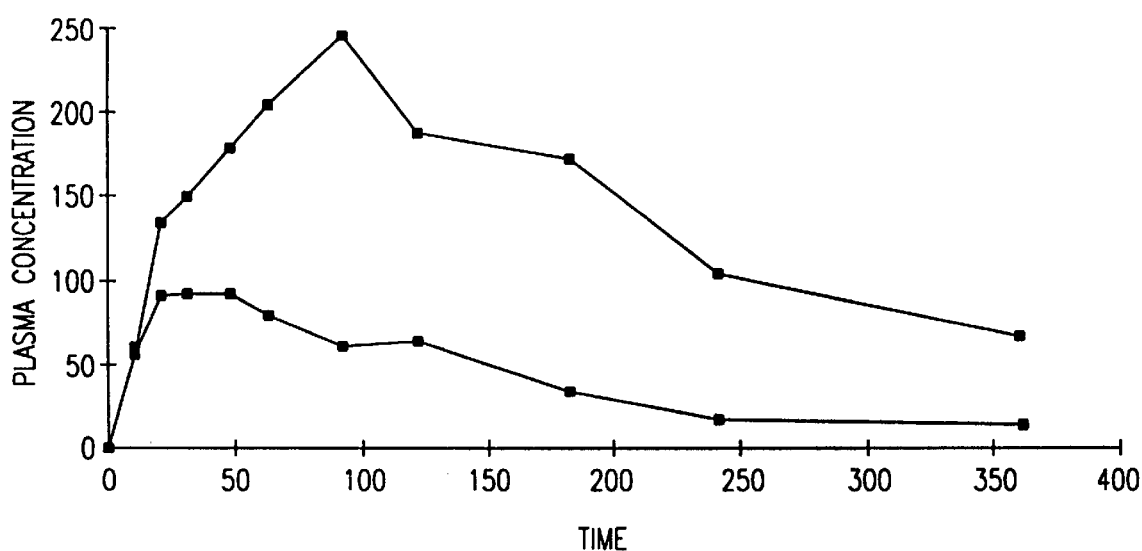
FIG. 2 is the plot of plasma concentration in ng/mL vs time in minutes following the oral administration to rats of a dose of 3 mg/kg of water-in-oil formulation BO and water-in-oil-in-water formulation B of the leutinizing hormone releasing hormone (LHRH) agent N-acetyl-D-2-naphthylalanyl-D-4-chlorophenylalanyl-D-3-pyridylalanyl-L-seryl-L-N-methyltyrosyl-D-$N^e$-nicotinoyllysyl-L-leucyl-L-$N^e$-isopropyllysyl-L-prolyl-D-alanylamide acetate. The upper curve represents formulation B and the lower curve represents formulation BO.
Figure 3:
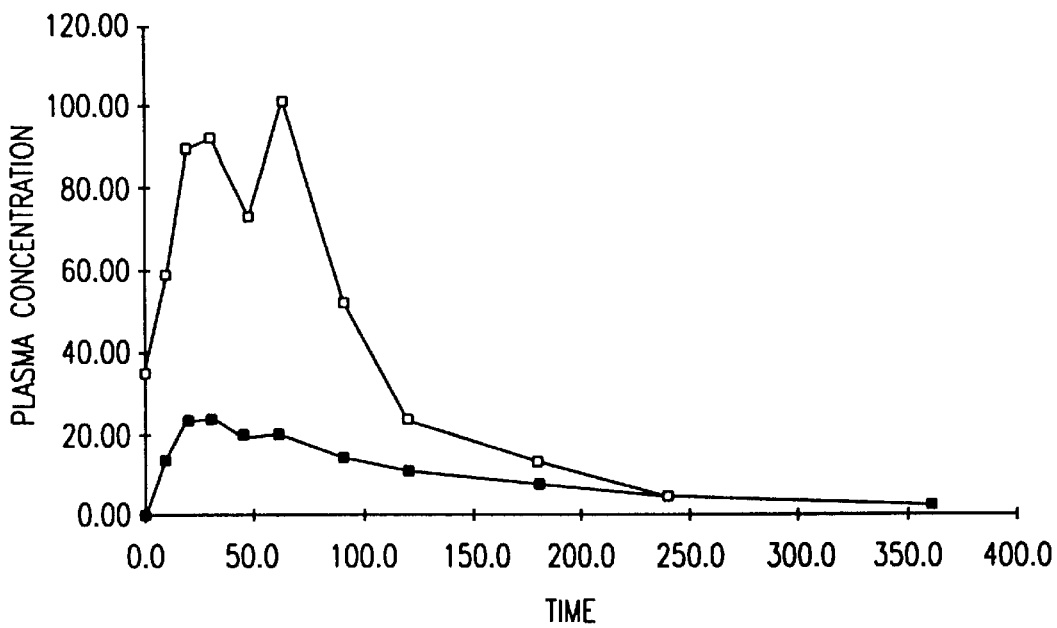
FIG. 3 is the plot of plasma concentration in ng/mL vs time in minutes following the oral administration to rats of a dose of 3 mg/kg of water-in-oil formulation HO and water-in-oil-in-water formulation H of the leutinizing hormone releasing hormone (LHRH) agent leuprolide acetate. The hollow squares represent formulation H and the filled-in squares represent formulation HO.

Drug oral bioavailiability was measured as described above for the water-in-oil formulations AO, BO HO and plotted against the drug bioavailability in the corresponding formulations A, B and H. The results are summarized in FIGS. 1–3. The data in FIGS. 1–3 show a substantial increase in drug bioavailability in the water-in-oil-in-water formulations over the water-in-oil formulations.

EXAMPLE 4

Comparison of Drug Partition Coefficients in Microemulsions and Aqueous Systems

Drug partition coefficients in aqueous solution and in water-in-oil emulsions were measured and the results summarized in Table 3. The compound is less soluble in oil than in water. It is believed that enhancing the lipid solubility of this drug would benefit its permeability and absorption following oral administration. The increased lipophilicity of the drug could also provide some protection of the drug from enzymatic deactivation as much of the peptide degradation that occurs in vivo does so in the aqueous environment of the gastrointestinal tract.

Individual aqueous solutions were prepared in a 100 mL volumetric flask. Partition mixtures were prepared by adding 1 mL of octanol to 1 mL of the aqueous solution containing microemuslion formulations in which drug is present at a concentration of 0.1 mg/ml. The mixtures were then vortexed for 2 minutes. After centrifugation at 2500 rpm, 0.2 mL aliquots of the aqueous phase were transferred to a clean culture tube for HPLC analysis.

Drug partition coefficients were determined by adding 0.1 mL of the formulations containing 5 mg/mL of drug prepared as in Example 1 to either 1 mL of pH 7.2 phosphate buffer or 1 mL of 0.1N HCl solution. The mixtures were vortexed for about one minute and aliquouts of the aqueous phase were removed and analyzed as described above.

TABLE 3

Partition Coefficients in Microemulsions and Aqueous Systems

| Formulation Composition | | Partition Coefficients | |
|---|---|---|---|
| ID | Ion pair | Oil/0.1N HCl | Oil/pH 7.2 Phosphate buffer |
| aqueous | — | 0 | 3.3 |
| AO | SDS | 500 | ∞ |
| BO | SDS | 143 | 100 |
| DO | SDS | 1.1 | 167 |
| EO | None | ∞ | 828 |
| FO | None | 0.1 | 0.16 |

The data in Table 3 show that the oil-water partition coefficient is significantly enhanced in the microemulsion formulations. Comparison of formulations AO and EO demonstrates that solubility of drug in pH 7.2 phosphate buffer and 0.1N HCl respectively is reduced to insignificance in the presence of 5 molar equivalents of sodium decanesulfonate, thereby indicating that substantial increases in lipohilicity can be attained by converting the drug to the decanesulfonate ion pair.

EXAMPLE 5

Particle Size of Microemulsion Formulations

In order to prepare microemulsions which are stable, clear to translucent in color, and which do not separate on standing it is desirable to have droplet diameters of less than one micron. It is also crucial that droplet size does not increase substantially in the acidic environment of the gut, as an increase in surface area of the particle exposes more of the drug to mucosal degradation.

Particle size distribution of the microemulsions was determined using a Nicon light scattering particle counter. To perform this test, a small amount of concentrated emulsion was dispersed in deinized water or 0.1N HCl solution immediately prior to size analysis.

TABLE 4

Mean Particle Size in Microemulsion Formulations

| | Mean Particle Size (nm) | | | |
|---|---|---|---|---|
| | O/W Ratio 1/5 | | O/W Ratio 1/10 | |
| Formulation | Water | 0.1N HCl | Water | 0.1N HCl |
| A | 163 | 851 | 154 | 355 |
| B | 145 | 167 | 166 | 189 |
| C | 160 | 198 | 180 | 182 |

The data indicate that the microfluidizer homogenization process satisfactorily reduced mean droplet size to the nanometer range. The particle size did not change substantially or become larger than about 1 mm in acid solution (simulated gastric fluid).

EXAMPLE 6

Protection of Leuprolide Acetate from Enzymatic Degradation in Emulsion Formulations Systemic absorption of peptide drugs can be increased by formulations which protect the drug from degradation in the gastrointestinal lumen. The protection of leuprolide acetate in the emulsion formulation HO from enzymatic degradation using a mucosal preparation of rat small intestine was investigated as described below.

Preparation of Rat Small Intestine Mucosa:

Rats were fasted overnight and then euthanized by $CO_2$ inhalation. The small intestinal segment was immediately removed, washed with cold normal saline, and then excised and rinsed with buffer M (50 mM Tris-HCl, pH 7.4, containing 0.25M sucrose and 1.0 mM dithiothreitol). The mucosal tissue of rat small intestine was scraped off gently with a surgical blade. The tissue scrapings were homogenized in 4–6M buffer M at 4° C. using a Teflon-glass homogenizer. The homogenate was centrifuged at 3,020×g for 10 minutes at 4° C. to remove cellular and nuclear debris. The resulting supernatant, which contained cytosol and relevant plasma and intracellular membrane fractions, was used for this study. The protein concentration was determined using a dye-binding assay with bovine serum albumin as standard according to the method of Bradford, M., *Anal. Biochem.*, 1976, 72, 248–254.

Figure 4:
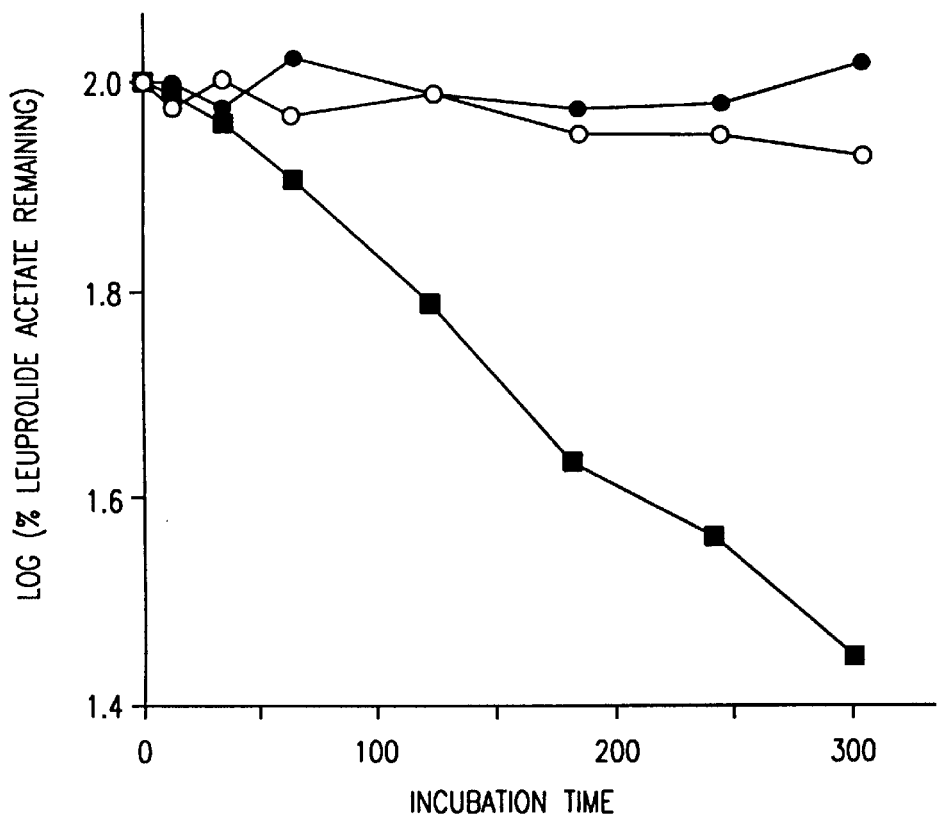
FIG. 4 is a plot of the log % leuprolide acetate remaining vs. incubation time in minutes following addition of rat intestinal mucosal preparation for leuprolide acetate formulation HO. Reactions were performed at 37° C. for 5 hours in a total volume of 100 $\mu$l containing 50 mM Tris-HCl, pH 7.4, 1 mM DTT, 100 $\mu$g mucosal preparation, and 50 $\mu$g leuprolide acetate. The filled in circles represent leuprolide acetate with no mucosal preparation. The hollow circles represent leuprolide acetate formulation HO+mucosal preparation. The filled-in squares represent leuprolide acetate+mucosal preparation.

Enzymatic Degradation of Leuprolide Acetate:

Reactions were performed at 37° C. for 5 hours in a total volume of 100 μl containing 50 mM Tris-HCl, pH 7.4, 1 mM DTT, 100 μg mucosal preparation, and 50 μg leuprolide acetate. The reaction was initiated by adding mucosal preparation. Aliquots were removed at various times (0, 10, 30, 60, 120, 180, 240, and 300 min.) and quenched with ice-cold acetonitrile. The mixture was centrifuged at 3,000 rpm for 5 minutes and filtered with 0.2 μm Millipore filters. The peptide concentrations in the filtrate were determined by HPLC as described by Sutherland, et al., *J. Liq. Chromatogr.*, 1987,10, 2281–2289. As shown in FIG. 4, the concentration of leuprolide acetate was not significantly decreased during 5 hours of incubation of the emulsion formulation HO with rat intestine mucosa.

The foregoing examples are presented for purposes of illustration and are not intended to limit the scope of the invention. Variations and changes which are obvious to one skilled in the art are intended to be within the scope and nature of the invention as defined in the appended claims.

We claim:

1. A uniform dispersion of droplets in aqueous medium, suitable for oral administration, the droplets comprising a core comprising between about 2% volume by volume to about 10% volume by volume water, between about 2% volume by volume to about 10% volume by volume of a non-toxic $C_2$–$C_5$ alkanol, between about 1 mg/ml to 10 mg/ml of a water soluble drug selected from the group consisting of agonists and antagonists of luteinizing hormone releasing hormone (LHRH), inhibitors of renin, and modulators of anaphylatoxin biologic factors, and a pharmaceutically acceptable salt thereof;

between about 10% volume by volume to about 50% volume by volume of a surfactant, and a coating surrounding the core comprising between about 20% volume by volume to about 50% volume by volume one or more pharmaceutically acceptable oils, based upon the volume of the droplet, wherein the total volume of the droplets comprises from about 10% to about 30% the total volume of the dispersion, said droplets having a mean particle size of less than one micron in diameter.

2. A uniform dispersion according to claim 1 wherein the aqueous medium comprises water and from about 2% v/v to about 20% v/v of surfactant based upon the volume of the aqueous medium.

3. A uniform dispersion according to claim 2 wherein the the mean particle diameter of the droplets is from about 50 nM to about 200 nM.

4. A uniform dispersion according to claim 1 wherein the droplets further comprise an ion-pair forming reagent wherein the mole ratio of ion-pair forming reagent to drug is from about 2:1 to about 10:1.

5. A uniform dispersion according to claim 4 wherein the water soluble drug is an agonist or antagonist of LHRH or a pharmaceutically acceptable salt thereof.

6. A uniform dispersion according to claim 5 wherein the water soluble drug is selected from the group consisting of N-acetyl-D-2-naphthylalanyl-D-4-chlorophenylalanyl-D-3-pyridylalanyl-L-seryl-L-N-methyltyrosyl-D-$N^e$-nicotinoyllysyl-L-leucyl-L-$N^e$-isopropyllysyl-L-prolyl-D-alanylamide acetate, leuprolide, and N-(S)-tetrahydrofur-2-oyl-glycyl-D-(3-(napth-2-yl)alanyl)-D-(3-(4-chlrophenyl)alanyl)-D-3-(pyrid-3-yl)alanyl-seryl-N-methyltyrosyl-($N^e$-nicotinyl)lysyl-leucyl-($N^e$-isopropyl)lysyl-prolyl-D-alanylamide, or a pharmaceutically acceptable salt thereof.

7. A uniform dispersion in aqueous medium of droplets according to claim 6 wherein the droplets comprise (a) 1–10 mg/mL of drug, (b) an ion-pair forming reagent wherein the mole ratio of ion-pair forming reagent to drug is from about 2:1 to about 10:1, (c) about 2% v/v to about 10% v/v of $C_2$–$C_5$ alkanol, (d) about 10% v/v to about 2% v/v of water, (e) between about 20% v/v to about 50% v/v of surfactant, (f) between about 20% v/v to about 50% v/v of pharmaceutically acceptable oil, (g) between about 5% v/v and about 10% v/v of oral mucosal membrane transport enhancing agent, and (h) between about 5% v/v and about 25% v/v of antioxidant wherein the volume percentages are based on the total volume of the droplets.

8. A uniform dispersion according to claim 7 wherein the non-toxic $C_2$–$C_5$ alkanol is ethanol.

9. A uniform dispersion according to claim 7 wherein the surfactant is oleic acid or laureth.

10. A uniform dispersion according to claim 7 wherein the ion forming reagent is sodium decanesulfonate.

11. A uniform dispersion according to claim 7 wherein the pharmaceutically acceptable oil is olive oil.

* * * * *